US006521640B1

(12) United States Patent
Gwag et al.

(10) Patent No.: US 6,521,640 B1
(45) Date of Patent: Feb. 18, 2003

(54) METHOD FOR INTERVIEWING NEURONAL DEATH USING SULFASALAZINE

(75) Inventors: Byoung Joo Gwag, Seoul (KR); Young Ae Lee, Kyunggi-do (KR); Bo Rum Ryu, Kyunggi-do (KR)

(73) Assignee: Neurotech Co., Ltd., Kyunggi-do (KR)

( * ) Notice: Subject to any disclaimer, the term of this patent is extended or adjusted under 35 U.S.C. 154(b) by 0 days.

(21) Appl. No.: 09/556,525

(22) Filed: Apr. 21, 2000

(30) Foreign Application Priority Data

Mar. 28, 2000 (KR) .......................................... 2000/15760

(51) Int. Cl.⁷ ............................................ A61K 31/445
(52) U.S. Cl. ....................................................... 514/327
(58) Field of Search .......................................... 514/327

(56) References Cited

FOREIGN PATENT DOCUMENTS

| WO | WO 98/20864 | 5/1998 |
| WO | WO 99/49860 | 10/1999 |

OTHER PUBLICATIONS

Wahl, C. et al., "Sulfasalazine: a Potent and Specific Inhibitor of Nuclear Factor Kappa B", J. Clin. Invest., vol. 101. No. 5, pp. 1163–1174, Mar. 1998.*
Zeidman, S. M. et al, "Clinical Applications of Pharmacologic Therapies for Spinal Cord Injury", Journal oof Spinal Disorders, vol. 9, No. 5, pp. 367–380, 1996.*
Choi, D. W. et al, Zinc and Brain Injury. *Ann. Rev. Neurosci* 21: 347–75 (1998).
Davis, S. et al, Selfotel in Acute Ischemic Stroke: Possible Neurotoxic Effects of an NMDA Antagonist. *Stroke* 31:347–354 (2000).
Goodman & Gillman, *The Pharmacological Basis of Therapeutics,* 10th ed., 1048–50, 1174–75, Mcgraw hill, New York(2001).
Korompilias, A., et al., (Abstract) Actions of glucocorticosteroids on Ischemic–reperfused Muscle and Cutaneous Tissue, *Microsurgery* 17(9):495–502 (1996).
Lees, K., Cerestat and other NMDA Antagonists in Ischemic Stroke. *Neurology* 49(S4):S66–69 (1997).
Mackenzie, I., Postmortem Studies of the Effect of Anti–inflammatory Drugs on Alzheimer–type Pathology and Associated Inflammation. *Neurobiology of Aging* 22:819–822(2001).
McGeer, P., The Inflammatory Response System of Brain: Implications for Therapy of Alzheimer and other Neurodegenerative Diseases. *Brain Research Reviews* 21:195–218 (1995).
Olney, J., Pathological Changes Induced in Cerebrocortical Neurons by Phencyclidine and Related Drugs. *Science* 244:1360–1362 (1989).

Rogawski, M., Low Affinity Channel Blocking (uncompetitive) NMDA Receptor Antagonists as Therapeutic Agents–toward an Understanding of Their Favorable Tolerability. *Amino Acids* 19:133–149. (2000).
Augustin et al., Chir. Forum Exp. Klin. Forsch. (1991), 437–441 (Abstract).
Grisham, M.B., Biochem. Pharmacol. (1990), 39 (12), pp. 2060–2063.
Williams et al., Gut (1989) vol. 30 (11), pp. 1581–1587.
Anderson and Hall, *Ann.Emerg.Med.* 22:987–992 (1993).
Anderson, Swartzwelder, and Wilson, *J.Neurophysiol.* 57:1–21 (1987).
Beal, *Ann.Neurol.* 38:357–366 (1995).
Beal, Ferrante, Swartz, and Kowall. *J.Neurosci.* 11:1649–1659 (1991).
Beal, Kowall, Ellison, Mazurek, Swartz, and Martin, *Nature* 321:168–171 (1986).
Brouillet and Beal. *Neuroreport.* 4:387–390 (1993).
Browne, Ferrante, and Beal, *Brain Pathol.* 9:147–163 (1999).
Bush, Pettingell, Multhaup, Paradis, Vonsattel, Gusella, Beyreuther, Masters, and Tanzi, *Science* 265:1464–1467 (1994).
Chan, *Stroke* 27:1124–1129 (1996).
Choi; *Neursci* 21:347–375 (1988).
Choi; *Neuron* 1:623–634 (1988).
Choi and Rothman, *Annu Rev Neurosci* 13:171–182 (1990).
Choi; *J Neurosci* 7:369–379, 1987.
Cuajungco; *Brain Research Reviews* 23:219–236 (1997).
Demediuk, Daly, and Faden. J Neurochem J. *Neurochem.* 52:1529–1536 (1989).
Dingledine, McBain, and McNamara, *Trends.Pharmacol.Sci.* 11:334–338 (1990).
Eisen and Weber, *Drugs Aging* 14:173–196 (1999).
Faden, Demediuk, Panter, and Vink., *Science* 244:798–800 (1989).
Faden, Lemke, Simon, and Noble. *J.Neurotrauma.* 5:33–45(1988).
Faden, *Pharmacol.Toxicol.* 78:12–17 (1996).
Frederickson, Hernandez, and McGinty. *Brain Res.* 480:317–321 (1989).
Goldberg and Choi, 1993, J Neurosci. 13:3510–3524.
Goodman & Gilman's The Pharmacological Basis of Therapeutics, Joel G. Hardman et al., eds., 9$^{th}$ edition, 1996, The McGraw–Hill Companies, pp 617–631 & 1059–1062.
Grundman, *Am.J.Clin.Nutr.* 71:630S.–636S (2000).
Gwag BJ, Lobner D, Koh JY, Wie MB, and Choi DW, 1995, Neuroscience. 68:615–619.

(List continued on next page.)

Primary Examiner—Dwayne C. Jones
(74) Attorney, Agent, or Firm—Shanks & Herbert

(57) ABSTRACT

The present invention provides a new of sulfasalazine as a potent agent for the treatment of neuronal death.

11 Claims, 10 Drawing Sheets

OTHER PUBLICATIONS

Hall and Braughler, *Free Radic.Biol.Med.* 6:303–313 (1989).
Hall, Braughler and McCall, *J. of Neurotrauma.* 5:81–89 (1988).
Hall, *Neurosurg.Clin.N.Am.* 8:195–206 (1997).
Holmes, *Cleve.Clin.J.Med.* 62:240–247(1995).
Ikonomidou, Qin, Labruyere, and Olney *J.Neuropathol.Exp.Neurol.* 55:211–224 (1996).
Jenner and Olanow, *Neurology* 47:S161–S170 (1996).
Jenner, *Pathol. Biol. (Paris.)* 44:57–64 (1996).
Joo, et al, *IOVS* 40:713–720 (1999).
Kass, Chambers, and Cottrell, *Exp.Neurol.* 103:116–122 (1989).
Kim, et al, *European Journal of Neuroscience,* 11:327–334 (1999).
Koh and Choi, J Neurosci Methods 20:83–90, 1987.
Koh, Peters, and Choi, *Science* 234:73–76 (1986).
Koh, Suh, Gwag, He, Hsu and Choi, *Science* 272: 1013–1016 (1996).
Lakowski, Hekimi, *Science* 272. 1010–1016 (1996).
Lange, Loschmann, Sofic, Burg, Horowski, Kalveram, Wachtel, and Riederer, *Naunyn Schmiedebergs Arch.Pharmacol.* 348:586–592 (1993).
Lee, Zipfel, and Choi, *Nature* 399:A7–A14 (1999).
Love, *Brain Pathol.* 9:119–131 (1999).
Marin, Papa, Engber, Bonastre, Tolosa, and Chase, *Brain Res.* 736:202–205 (1996).
McNamara, Russell, Rigsbee, and Bonhaus, *Neuropharmacology* 27:563–568 (1988).
Merello, Nouzeilles, Cammarota, and Leiguarda. *Clin. Neuropharmacol.* 22:273–276 (1999).
Minta, Koa, Tsien, *J. of Biological Chemistry* vol. 264 14:8171–8178 (1989).
Montastruc, et al, *Neuroscience and Biobehavioral Reviews,* vol. 21 No. 4:477–480 (1997).
Okiyama, Smith, White, Richter, and McIntosh. *J.Neurotrauma.* 14:211–222 (1997).
Papa and Chase, *Ann.Neurol.* 39:574–578 (1996).
Park, Nehls, Graham, Teasdale, and McCulloch, *Ann Neurol* 24:543–551 (1988).
Prasad, Cole, and Kumar. *J.Am.Coll.Nutr.* 18:413–423 (1999).
Rosen, Siddique, Patterson, Figlewicz, Sapp, Hentati, Donaldson, Goto, O'Regan, and Deng. *Nature* 362:59–62 (1993).
Rothstein. *Clin.Neurosci.* 3:348–359 (1995).
Schroder and Campbell, *Clin.Pharmacol.Ther.* 13:539–551 (1972).
Siesjo and Siesjo, *Eur.J.Anaesthesiol.* 13:247–268(1996).
Simon, Swan, Griffiths, and Meldrum. *Science* 226:850–852 (1984).
E. H. Sinz et al, *J. of Cerebral Blood Flow and Metabolism* 18:610–615 (1998).
Smith, Dawson, and Swan, *Gut* 20:802–805 (1979).
Smith, Harris, Sayre, and Perry, *Proc.Natl.Acad.Sci.U.S.A.* 94:9866–9868 (1997).
Stenson and Lobos, J. clin. Invest. 69, 494 (1982).
Suh, Chen, Motamedi, Bell, Listiak, Pons, Danscher, and Frederickson, *Brain Res.* 852:268–273 (2000).
Suh, Jensen, Jensen, Silva, Kesslak, Danscher, and Frederickson. *Brain Res.* 852:274–278 852 (2000).
Verhagen, Del Dotto, Natte, van den Munckhof, and Chase, *Neurology* 51:203–206 (1998).
Wahl, Liptay, Adler, and Schmid. *J.Clin.Invest.* 101:1163–1174 (1998).
Weiss JH, Hartley DM, Koh JY, Choi DW, 1993, Neuron. 10:43–49.
Weiss, Goldberg, and Choi, *Brain Res.* 380:186–190 (1986).
Wieloch, *Science* 230:681–683 (1985).
Won, *Neurobiology of Disease* 7:1–9 (2000).
Wong, Coulter, Choi, and Prince. *Neurosci.Lett.* 85:261–266 (1988).
Zeidman, Ling, Ducker, and Ellenbogen, *J.Spinal.Disord.* 9:367–380 (1996).

\* cited by examiner

SULFASALAZINE | 2-HYDROXY-5-[4-[(2-PYRIDINYLAMINO) SULFONYL | AZO | BENZOIC ACID|

METHOD FOR INTERVIEWING NEURONAL DEATH USING SULFASALAZINE

FIELD OF THE INVENTION

The present invention is related to a new use of sulfasalazine, and in particular, is related to a method for preventing neuronal death in brain diseases by administering sulfasalazine.

BACKGROUND OF THE INVENTION

<Excitotoxicity and Brain Diseases>

Excess activation of ionotropic glutamate receptors sensitive to N-methyl-D-asparte (NMDA receptors) produces neuronal death and has been known to mediate various neurological diseases [Choi, Neuron 1:623–634 (1988)]. Glutamate, an excitatory neurotransmitter, is massively accumulated in brain subjected to hypoxic-ischemic injuries, which activates ionotropic glutamate receptors permeable to $Ca^{2-}$ and $Na^+$ and then causes neuronal death [Choi and Rothman. Annu Rev Neurosci 13:171–182 (1990)]. Antogonists of NMDA receptors remarkably attenuate brain injury following hypoclycemia, hypoxia, or hypoxic-ischemia [Simon, Swan, Griffiths, and Meldrum. Science 226:850–852 (1984); Park, Nehls, Graham, Teasdale, and McCulloch, Ann Neurol 24:543–551 (1988); Wieloch, Science 230:681–683 (1985); Kass, Chambers, and Cottrell, Exp. Neurol, 103:116–122 (1989); Weiss, Goldberg, and Choi, Brain Res. 380:186–190 (1986)]. Thus, NMDA receptor antagonists possess therapeutic potentials to protect brain against hypoglycemia, hypoxia, and hypoxic-schemic injuries.

Excitotxicity appears to contribute to neuronal degeneration following traumatic brain injury (TBI). Levels of quinolinic acid, an endogenouis agonist of NMDA receptors, are increased 5- to 50-fold in human patients with TBI [E. H. Sinz, P. M. Kochanek, M. P. Heyes, S. R. Wisniewski, M. J. Bell, R. S. Clark, S. T. DeKosky, A. R. Blight, and D. W. Marion]. Quinolinic acid is increased in the cerebrospinal fluid and associated with mortality after TBI in humans [J. Cereb. Blood Flow Metub. 18:610–615, (1998)]. In animal models of brain trauma, levels of glutamate and aspartate were markedly increased. Faden, Demediuk, Panter, and Vink [Science 244:798–800 (1989)]. Glutamate release was also observed in rat spinal cord following impact trauma [Demediuk, Daly, and Faden. J Neurochem J. Neurochem. 52:1529–1536 (1989)]. NMDA receptor antagonists attenuate neuronal death following traumatic brain or spinal cord injuries [Faden, Lemke, Simon, and Noble. J. Neurotrauma. 5:33–45(1988); Okiyama, Smith, White, Richter, and McIntosh. J. Neurotrauma. 14:211–222 (1997)].

Glutamate plays a central role in the induction and the propagation of seizures. Dingledine, McBain and McNamara [Trends. Pharamacol. Sci. 11:334–338 (1990); Holmes. Cleve. Clin. J. Med. 62:240–247(1995)]. NMDA receptor antagonists were shown to act as anticonvulsants and antiepileptogenic drugs in various models of epilepsy [Anderson, Swartzwelder, and Wilson, J. Neurophysiol. 57:1–21 (1987); Wong, Coulter, Choi, and Prince. Neurosci. Lett. 85:261–266 (1988); McNamara, Russel, Rigsbee, and Bonhaus, Neuropharmacology 27:563–568 (1988)].

Amyotrophic lateral sclerosis (ALS) is accompanied by degeneration of both upper and lower motor neurons and marked neurogenic atrophy, weakness, and fasciculation. While the pathogenesis of ALS remains to be resolved, excitotoxicity has been expected to participate in the process of ALS. In particular, ALS patients show increased levels of extracellular glutamate and defects in glutamate transport. Administration of excitotoxins mimicked pathological changes in the spinal cord of ALS patients [Rothstein. Clin. Neurosci. 3:348–359 (1995); [konomidou, Qin, Labruyere, and Olney J. Neuropahol. Exp. Neurol. 55:211–224 (1996)].

Antagonizing NMDA receptors appears to be applied to treat Parkinson's disease (PD). Several antagonists of NMDA receptors protect dopaminergie neurons from the neurotoxin MPTP (1-methyl-4-phenyl-1,2,3,6-tetrahydropyridine) [Lange, Losehmann, Sofie, Burg, Horowski, Kalveram, Wachel, and Riederer, Naunym Schmiedebergs Arch. Pharmacol. 348:586–592 (1993); Brouillet and Beal. Neuroreport. 4:387–390 (1993)]. NMDA receptor antagonists also ameliorate levodopa-induced dyskinesia and thus can improve the therapeutic effects of levodopa [Papa and Chase. Ann. Neurol. 39:574–578 (1996) Marin, Papa, Engber, Bonastre, Tolosa, and Chase. Brain Res. 736:202–205 (1996)]. Two NMDA receptor antagonists, memantine and dextromethophan, have been proved beneficial in treating PD patients [Verhagen, Del Dotto, Natte, vand den Munekhof, and Chase, Neurology 51:203–206 (1998); Merello Nouzeilles, Cammarota, and Leiguarda, Clin. Neuropharmacol. 22:273–276 (1999)].

Huntington's disease (HD) is a progressive neurodegenerative disease predominantly affecting small- and medium-sized interneurons but sparing NADPH-diaphorase neurons containing somatostatin and neuropeptide in the striata. These pathological features of HD are observed in the striatal tissues following the intrastriatal injections of quinolinic acid or cultured striatal neurons exposed to NMDA, raising the possibility that NMDA receptor-mediated neurotoxicity contributes to selective neuronal death in HD [Koh, Peters, and Choi, Science 234:73–76 (1986)]. Beal, Kowall, Ellison, Mazurek, Swartz, and Martin, Nature 321:168–171 (1986); Beal, Ferrante, Swartz, and Kowall, J. Neurosci. 11:1649–1659 (1991)].

<Free Radicals and Brain Diseases>

Free radicals are produced in degenerating brain areas following hypoxic-ischemia or traumatic brain and spinal cord injuries [Hall and Braughler, Free Rudic. Biol. Med. 6:303–313 (1989); Anderson and Hall, Ann. Emerg. Med. 22:987–992 (1993); Siesjo and Siesjo, Eru. J. Anaesthesiol. 13:247–268(1996); Love, Brain Pathol 9:119–131 (1999)]. Antioxidants or maneuvers scavenging free radicals attenuate brain damages by hypoxic-ischemia or traumatic injuries [Faden, Pharmacol. Toxicol. 78:12–17 (1996); Zeidman, Ling, Ducker, and Ellenbogen, J. Spinal. Disord. 9:367–380 (1996); Chan, Stroke 27:1124–1129 (1996); Hall, Neurosurg. Clin, N. Am. 8:195–206 (1997)]. Extensive evidence supports that free radials can be produced in brain areas undergoing degeneration in neurodegenerative diseases possibly due to point mutations in Cu/Zn superoxide dismutase in ALS, decreased glutathione level and increased iron level in PD, accumulation of iron in AD, or mitochondrial dysfunction in HD [Rosen, Siddique, Patterson, Figlewicz, Sapp, Hentati, Donaldson, Goto, O'Regan, and Deng, Nature 362:59–62 (1993); Jenner and Olanow, Neurology 47:S161–S170 (1996); Smith, Harris, Sayre, and Perry, Proc. Natl. Acad. Sci. U.S.A. 94:9866–9868 (1997); Browne, Ferrante, and Beal, Brain Pathol. 9:147–163 (1999)]. Accordingly, antioxidants have been neuroprotective against such neurodegenerative diseases. Jenner, Pathol. Biol. (Paris.) 44:57–64 (1996); Beal, Ann. Neurol. 38:357–366 (1995); Prasad, Cole, and Kumar, J. Am. Cott. Nutr. 18:413–423 (1999); Eisen and Weber, Drugs Aging 14:173–196 (1999); Grundman, Am. J. Clin. Nutr. 71:630S–636S (2000)].

<Zine and Brain Diseases>

$Zn^{2+}$ mediates neurodegenerative process observed in seizure, ischemia, trauma, and Alzheimers diseases (AD). The central administration of kainate, a seizure-inducing excitotoxin, causes the translocation of $Zn^{2+}$ into postsynaptic degenerating neurons in several forebrain areas [Frederickson, Hernandez, and McGinty. Brain Res. 480:317–321 (1989)]. Blockade of $Zn^{2+}$ translocation with Ca-EDTA attenuates neuronal loss following a transient forebrain ischemia or traumatic brain injury [Koh, Suh, Gwag, He, Hsu, and Choi, Science 272: 1013–1016 (1996); Suh, Chen, Motamedi, Bell, Listiak, Pons, Danscher, and Frederickson, Brain Res. 852:268–273 (2000)]. $Zn^{2-}$ is observed in the extracellular plaque and degenerating neurons in AD, which likely contributes to neuronal degeneration in AD [Bush, Pettingell, Multhaup, Paradis, Vonsattel, Gusella, Beyreuther, Masters, and Tanzi, Science 265:1464–1467 (1994); Suh, Jensen, Jensen, Silva, Kesslak, Danscher, and Frederickson, Brain Res. 852:274–278 852 (2000)].

SUMMARY OF THE INVENTION

The present invention provides a method for preventing neuronal loss in stroke, trauma, epilepsy and neurodegenerative diseases.

The present invention provides a method for protecting central neurons from acute or chronic injuries to central nervous system(CNS), which comprises administering appropriate quantity and forms of sulfasalazine to a patient or a mammal suffering CNS injuries.

The present invention still provides a method for reducing neuronal death in CNS injuries by administering appropriate quantity and forms of sulfasalazine that prevents NMDA-, $Zn^{2+}$-, and free radical-mediated neurotoxicity simultaneously, said CNS injuries including ischemia, hypoxia, hypoglycemia, traumatic brain injury, traumatic spinal cord injury, epilepsy, Huntington's disease, Parkinson's disease, Alzheimer's disease, or Amyotrophic lateral sclerosis.

DETAILED DESCRIPTION OF THE INVENTION

Figure 1:
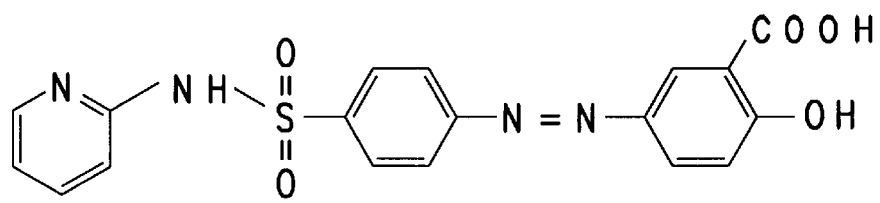
FIG. 1 is a drawing showing chemical structure of sulfasalazine.

The present invention is based on the finding that sulfasalazine prevents neuronal death induced by NMDA, $Zn^{2+}$ or free radicals. Sulfasalazine or salicylazosulfapyridine contains 5-aminosalicylic acid (mesalamine) linked covalently to sulfapyridine (FIG. 1). The novel neuroprotective action of sulfasalazine can be applied to reduce neuronal degeneration occurring in various neurological diseases.

Sulfasalazine is used for treatments of ulcerative colitis, regional enteritis, and rheumatoid arthritis. Sulfasalazine is cleaved to sulfapyridine and 5-aminosalicylate by bacteria in the colon. The latter is the active component in treating inflammatory bowel disease [Goodman & Gilman's The Pharmacological Basis of Therapeutics, Joel G. Hardman et al., eds., $9^{th}$ edition, 1996, The McGraw-Hill Companies, pps 617–631 & 1059–1062]. The present inventors show that sulfasalazine protects cultured cortical neurons devoid of bacteria, suggesting that sulfasalazine itself, not its metabolites, is neuroprotective. This is further supported by findings that 5-aminosalicylate up to 1,000 $\mu$M does not attenuate NMDA neurotoxicity.

Most of sulfasalazine's adverse effects are caused by sulfapyridine, a breakdown product of sulfasalazine. These side effects include Heinz-body anemia, agranulocytosis, nausea, and fever. As sulfasalazine, not its metabolites, prevents neuronal degeneration, the present inventors suggest appropriate delivery of sulfasalazine to target CNS areas in treating relevant neurological diseases. Thus, the potential side effects of sulfasalazine can be minimized.

Sulfasalazine acts as an immunosuppressant by inhibiting prostaglandin synthetase, lipoxygenase, activation of the transcription factor NF-kappa B [Smith, Dawson, and Swan, *Gut* 20:802–805 (1979); Stenson and Lobos, *J. clin. Invest.* 69, 494 (1982); Wahl, Liplay, Adler, and Schmid. *J. Clin. Invest.* 101:1163–1174 (1998)]. The present invention provides evidence that sulfasalazine acts as a direct neuroprotective agent by preventing NMDA-mediated excitotoxicity. $Zn^{2+}$ neurotoxicity, and free radical neurotoxicity. This neuroprotective action of sulfasalazine involves preventing influx and accumulation of $Ca^{2+}$ and $Zn^{2+}$ at doses of 30–1,000 $\mu$M and scavenging reactive oxygen species at doses of 3–100 $\mu$M.

The total daily dose of sulfasalazine in adults is 3–4 g initially and followed by 500 mg four times for maintenance. The serum concentrations of sulfasalazine reach to approximately 500 $\mu$M 3–5 hrs after oral ingestion of a single 4 g dose of sulfasalazine in man [Schroder and Campbell, *Clin. Pharmacol. Ther.* 13:539–551 (1972)]. Thus, sulfasalazine as a liphophilic molecule likely to pass the blood-brain barrier can be administered through oral ingestion or intravenous, intramuscular, and subcutaneous injections so as to treat acute and chronic brain diseases accompanied by excitotoxicity, $Zn^{2+}$ neurotoxicity, and free radical toxicity. These diseases include hypoxia, hypoglycemia, ischemia, traumatic brain injury, traumatic spinal cord injury epilepsy, Alzheimer's disease, Parkinson's disease, Huntington's disease, and Amyotrophic lateral sclerosis.

The present invention provides a method for protecting central neurons from acute or chronic CNS injuries, which comprises administering appropriate quantity and forms of sulfasalazine to a patient or a mammal suffering from CNS injuries. The CNS injuries are caused by activation of ionotropic glutamate receptors sensitive to N-methyl-D-aspartate (NMDA), by $Zn^{2+}$ entry and accumulation, or by hypoxia, hypoglycemia, ischemia, hypoxic-ischemia, traumatic brain injury, traumatic spinal cord injury, epilepsy, Alzheimer's disease, Parkinson's disease, Huntington's disease, and Amyotrophic lateral sclerosis.

According to the present invention, the CNS injuries result from the accumulation of $Ca^{2+}$ following activation of NMDA receptor. And sulfasalazine is preferred to its structural moieties, salicylate or 5-aminosalicylate, in attenuating NMDA neurotoxicity.

Sulfasalazine is effective to protect CNS injuries caused by free radicals, wherein the free radicals mediate neuronal death following CNS injuries. The free radical neurotoxicity is triggered by $Fe^{2+}$ (an agent producing hydroxyl radical via Fenton reaction) or buthionine sulfoximine (an agent depleting glutathione). In this regards, sulfasalazine prevents free radical toxicity by acting as an antioxidant.

For the present invention, sulfasalazine is effective to protect CNS injuries from hypoxic-ishemia, wherein neurons undergo degeneration following deprivation of oxygen and glucose. In this regards, the effects of sulfasalazine attenuating NMDA and free radical neurotoxicity are responsible for reducing neuronal injury following deprivation of oxygen and glucose. But, the present invention is not limited by any particular mechanism of action which sulfasalazine shows in light of central neuron protection.

For the present invention, the term of "protecting central neuron" means a prevention of neuronal death in CNS diseases.

Effective doses of sulfasalazine will depend upon what mediates neuronal death in acute and neurodegenerative diseases. To treat ischemia, hypoxia, hypoglycemia, traumatic brain injury, traumatic spinal cord injury, epilepsy, Huntington's disease, Parkinson's disease, or Amyotrophic lateral sclerosis, the serum concentrations of sulfasalazine after initial administration through oral ingestion or intravenous, intramuscular, and subcuttaneous injections should reach to approximately 0.1–10000 mg/kg (body weight), preferably about 3–100 mg/kg so as to prevent NMDA-, $Zn^{2+}$-and free radical-mediated neurotoxicity. For chronic use, the serum concentrations of sulfasalazine should be maintained approximately to 0.5–1000 mg/kg, preferably about 5–50 mg/kg. To treat Alzheimer's disease that free radical plays a crucial role in neurotoxicity, sulfasalazine can be administered primarily through oral ingestion but also through intravenous, intramuscular, and subcutaneous injections. In this situation, sulfasalazine should be chronically used in order to maintain the serum concentrations of sulfasalazine approximately to 0.1–100 mg/kg, preferably 1–30 mg/kg.

Sulfasalazine can be formulated into compositions. In addition to sulfasalazine, or as appropriate, pharmaceutically acceptable salt thereof, the composition can comprises a pharmaceutically acceptable carrier, which is well known to those of ordinary skill. The composition can be in a form suitable for, for example oral, intravenour or intramuscular administration.

The mammals to which sulfasalazine may be administered according to the present invention include, but not limited to, human beings, cats, dogs, poultry, cows and the like.

The following non-limiting working examples will explain in more detail the present invention, but they should not be interpreted to limit the present invention in any

EXAMPLES

Primary cortical cell cultrues from embryonic mice were prepared and used to examine neuroprotective action of compounds. Mouse cortical cell culture system has been extensively used to study mechanisms and pharmacological intervention of neuronal death in neurological diseases. In brief, mouse cerebral coritces were removed from brains of the 15 day—old—fetal mice, in accordance with a protocol approved by our institutional animal care committee. The neocortices were gently triturated and plated on 24 well plates (5 hemispheres/plate) precoated with 100 µg/ml poly-D-lysine and 4 µg/ml laminine. Plating media consist of Eagles minimal essential media (MEM, Earles salts, supplied glutamine-free) supplemented with 5% horse serum, 5% fetal bovine serum, 2 mM glutamine, and 21 mM glucose. Cultures were maintained at 37° C. in a humidified 5% $CO_2$ atmosphere. After 7 days in vitro (DIV 7), cultures were shifted into a growth medium identical to the plating medium but lacking fetal serum. At DIV 7–9, 10 mM cytosine arabinofuranoside was included to halt overgrowth of glia. Mixed cultures of neurons and glia were then fed twice a week.

To induce neuronal injury by NMDA or $Zn^{2+}$, cortical cell cultures were exposed to toxic doses of NMDA for 10 min or $Zn^{2+}$ for 30 min in a HEPES-buffered control salt solution (HCSS): (in mM) 120 NaCl, 5KCl, 1.6$MgCl_2$, 2.3 $CaCl_2$, 15 glucose 20 HEPES, and 10 NaOH. After exposure, cultures were washed out 3 times and exchanged with MEM adjusted to 25 mM glucose and 26.2 mM sodium bicarbonate, and placed in the $CO_2$ incubator for the next 20–24 hr.

To induce free radical neurotoxicity, cortical cell cultures were continuously exposed to $Fe^{2+}$ or BSO for 20–24 hr, in MEM adjusted to 25 mM glucose and 26.2 mM sodium bicarbonate.

Oxygen or glucose deprivation: cortical cell cultures (DIV 15–17) were transferred to an anaerobic chamber containing 5% $CO_2$, 10% $H_2$, and 85% $N_2$ as described before (Gwag B J, Lobner D, Koh J Y, Wie M B, and Choi D W, 1995, Neuroscience, 68:615–619). Briefly, cultures were placed in a hypoxia chamber flooded with 95% $N_2$ and 5% $CO_2$. Culture medium was then replaced with glucose-free deoxygenated balanced salt solution containing (in mM): 143.6 NaCl, 5.4 KCl, 1.8 CaCl, 0.8 $MgSO_4$, 1 $NaH_2PO_4$, 26.2 $NaHCO_3$, 5.5 glucose, and 10 mg/l, phenol red. The oxygen-glucose deprivation was terminated by addition of 5.5 mM glucose, and cultures were immediately transferred back into the $CO_2$ incubator. Neuronal injury was quantified 24 hr later.

Overall cell injury was assessed microscopically under phase-contrast optics or by measuring amount of lactate dehydrogenase (LDH) released into the bathing medium 24 hr after neurotoxic insults as previously described (Koh and Choi, J Neurosci Methods 20:83–90, 1987). The present neuronal death was normalized to the mean LDH value released 24 hr after continuous exposure to 500 µM NMDA (=100) or a sham control (=0).

Entry and accumulation of $Zn^{2+}$ into neurons were analyzed using TSQ (N-(6-methoxy-8-quinolyl)-p-toluene sulfonamide), a membrane-permeable $Zn^{2+}$-chelating dye (Weiss J H, Hartley D M, Koh J Y, Choi D W, 1993, Neuron, 10:43–49). Cultures were incubated in HCSS containing 0.01% TSQ for 5 min, observed under fluorescence microscopy with a UV filter (excitation 365 nm, dichroic 400 nm, barrier 450 nm), and the intensity of TSQ was analyzed using a fluorescence plate reader.

Levels of intracellular free $Ca^{2+}$ ($[Ca^{2+}]_i$) were analyzed using a $Ca^{2+}$ sensitive indicator flou-3 under a fluorescence microphotometry (Minta A. Kao J P. Tsien R Y. 1989, J Bio Chem. 264:8171–8178). Cortical cell cultures (DIV 13) grown on a glass-bottom dish were loated with 5 µM fluo-3 AM plus 2% Pluronic F-127 in HCSS solution for 30 min. Cultures were then challenged with 100 µM NMDA, alone or in the presence of 300 µM sulfasalazine. The fluorescent signal was observed on the stage of a Nikon Diaphot inverted microscope equipped with a 100 W xenon lamp, a filter (excitation 480 nm, emission 535 nm) and a Nikon 40X, 1.30 N.A. objective. The fluroescence images were analyzed using a QuantiCell 700 system (Applied Imaging, England).

To analyze $Ca^{2+}$ uptake, cortical cell cultures (DIV 13–14) were added with 300 µM NMDA and 1.5 µCi $^{45}Ca^{2+}$ for 10 min, washed thoroughly with HCSS, and lysed in 0.2% SDS. Levels of $^{45}Ca^{2+}$ in the lysates were read in a Beckman Scintillation counter.

To analyze reactive oxygen species in cortical cells, cortical cultures were loaded with 10 µM 6-carboxy-2',7'-dichlorodihydrofluorescein diacetate (DCDHF-DA) plus 2% Pluronic F-127 in HCSS solution containing (120 mM NaCl, 5 mM KCl, 1.6 mM $MgCl_2$, 2.3 mM $CaCl_2$, 15 mM Glucose, 20 mM HEPES, 10 mM NaOH) for 20 minutes at 37° C., washed three times with HCSS solution, and the fluorescence signal of DCF (Ex 1=488 nm, Em 1=510 nm), the oxidation product of DCDHF-DA, was analyzed on the stage of a Nikon Diaphot inverted microscope equipped with a 100W Xenon lamp and a Nikon 20X, 0.4 N.A. objective.

Example 1. Neuroprotective effects of sulfasalazine against NMDA-mediated excitotoxicity Sulfasalazine prevents excitotoxicity.

Figure 2:
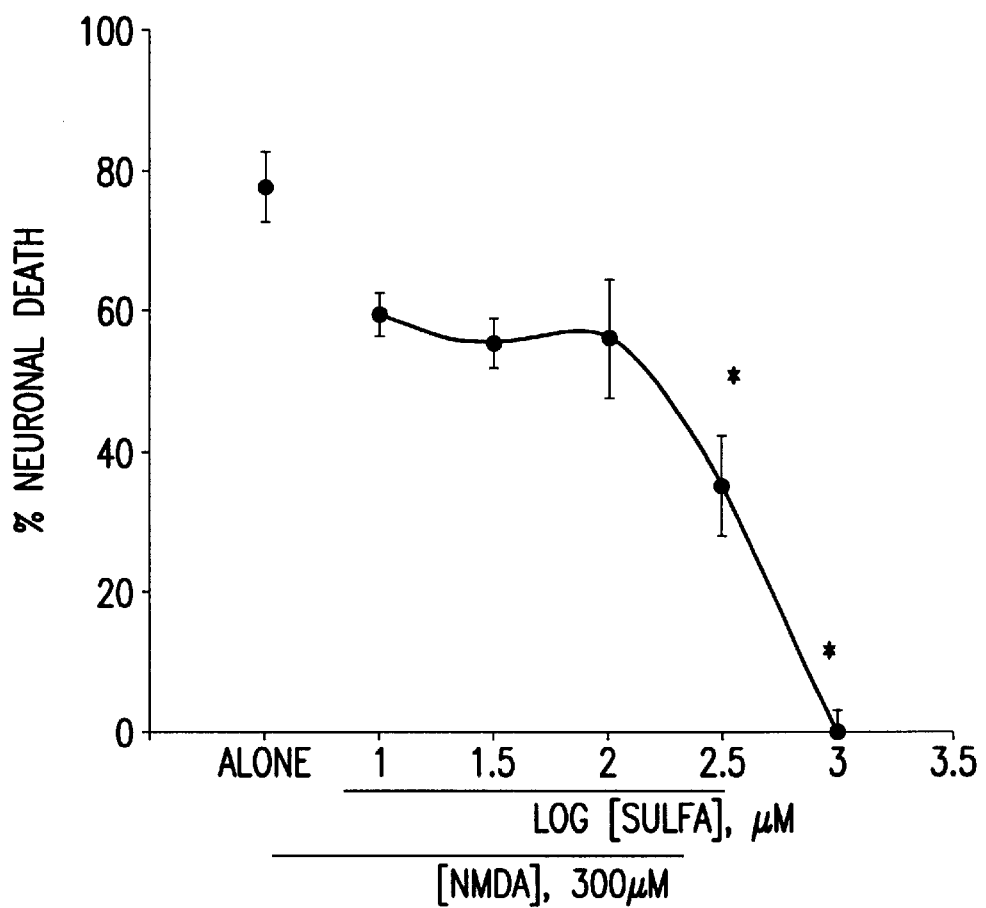
FIG. 2 is a graph plotting a dose-response effect of sulfasalazine against neuronal death 24 hr following a brief exposure to 300 μM NMDA. Cocultures of mouse cortical neurons and glia (DIV 12–14) were exposed to 300 μM NMDA for 10 min, alone or with inclusion of 10–1000 μM sulfasalazine. Neuronal death was analyzed by measuring LDH efflux into the bathing medium 24 hr later, mean ± S.E.M. (n=8–16 cultrues per condition), scaled to the mean LDH value corresponding to the near-complete neuronal death induced by 24 hr exposure to 500 μM NMDA (=100%). Asterisk indicates significant difference from relevant control (NMDA alone), at $\rho<0.05$ using ANOVA and Student-Neuman-Keuls' test.
Figure 3:
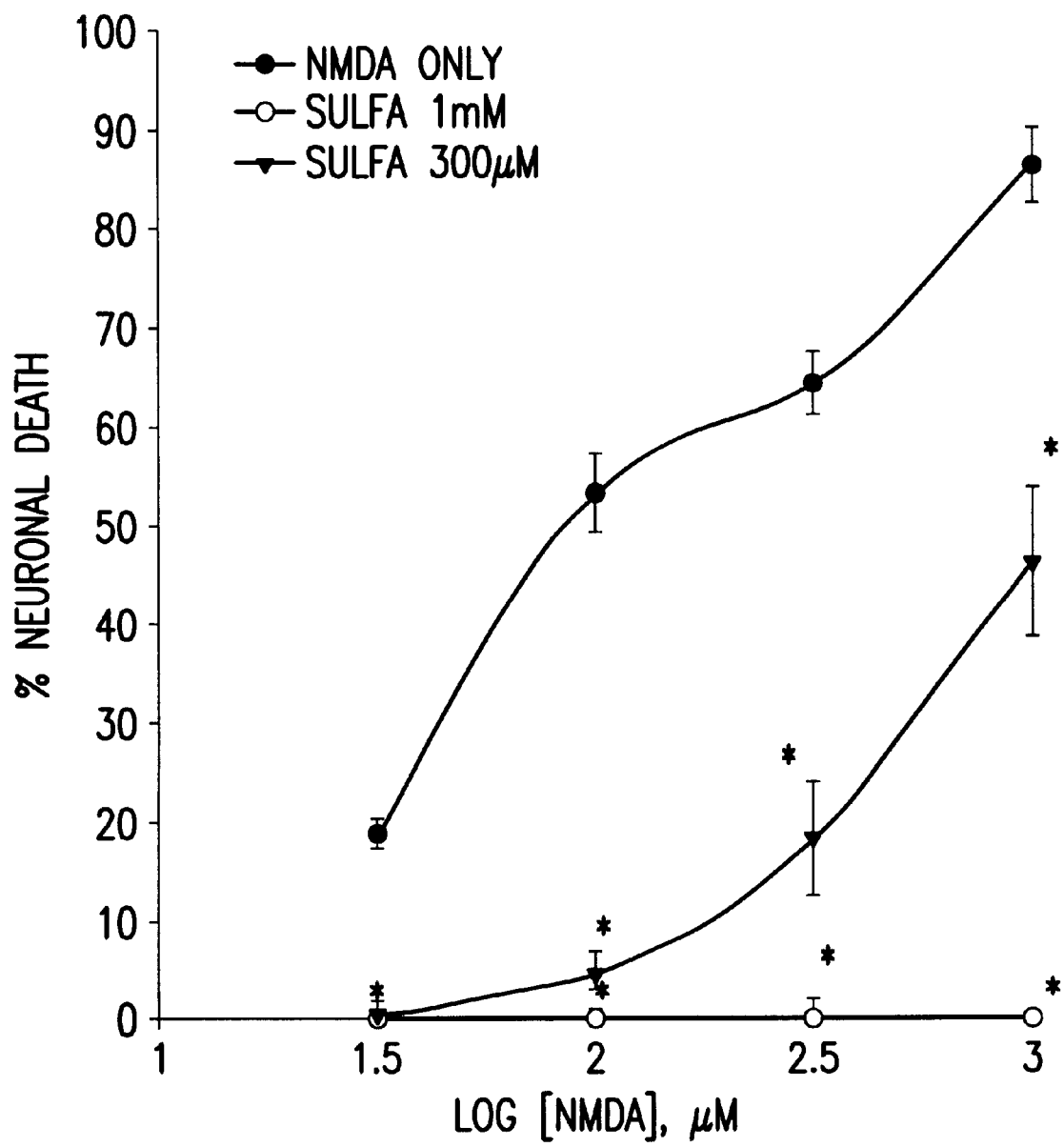
FIG. 3 is a graph plotting neuroprotective effects of sulfasalazine against dose-dependent neurotoxicity by NMDA. Cortical cell cultures were exposed to 30–1000 μM NMDA for 10 min, alone or in the presence of 300 or 1000 μM sulfasalazine. Neuronal death was analyzed by measuring LDH efflux into the bathing medium 24 hr later, mean ± S.E.M. (n=8–16 cultures per condition). Asterisk indicates significant difference from relevant control (NMDA alone), at $\rho<0.05$ using ANOVA and Student-Neuman-Keuls' test.

Cocultures of cortical neurons and glia (DIV 12–14) underwent widespread neuronal death 24 hr following a brief exposure to 300 µM NMDA for 10 min (FIG. 2) This NMDA-induced neuronal death was attenuated by concurrent addition of sulfasalazine in a dose-dependent manner. Inclusion of 100–300 µM sulfasalazine partially reduced NMDA neurotoxicity. With inclusion of 1 mM sulfasalazine, NMDA neurotoxicity was completely blocked (FIG. 2). Increasing doses of NMDA up to 1 mM did not interfere with the neuroprotective effects of sulfasalazine, suggesting that sulfasalazine non-connectively prevents NMDA neurotoxicity (FIG. 3).

Figure 4:
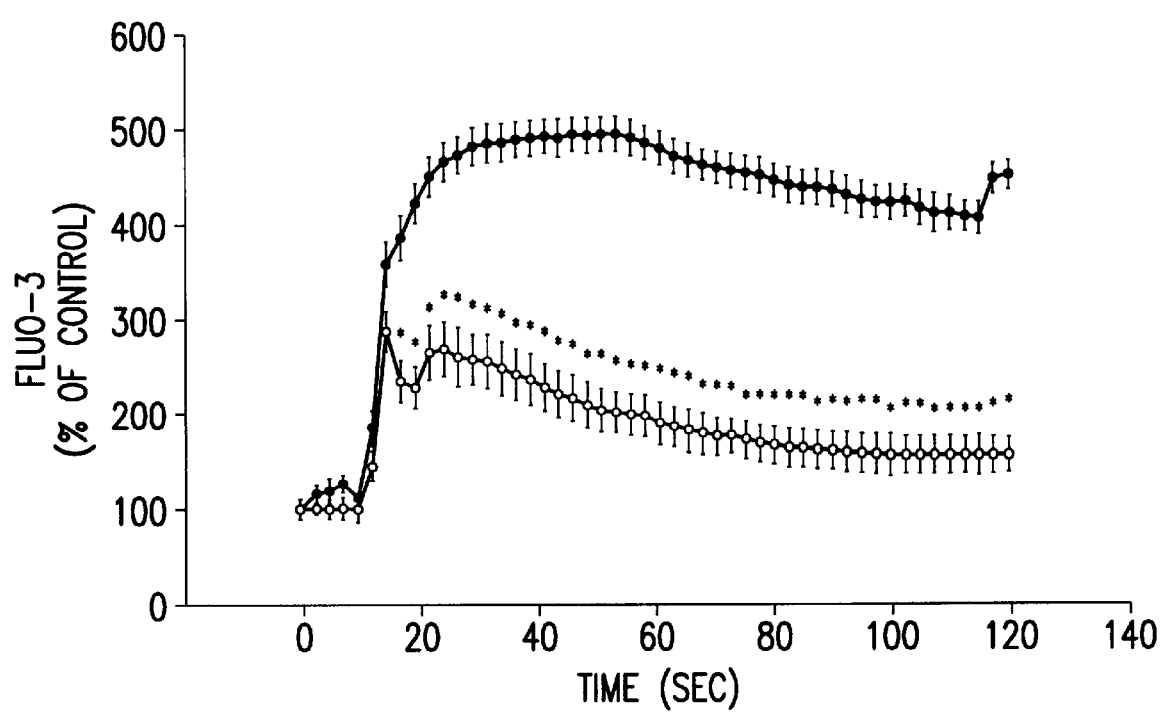
FIG. 4 is a graph plotting effects of sulfasalazine against NMDA-induced accumulation of intracellular free $Ca^{2+}$. Cortical cell cultrues (DIV 12) were exposed to a sham wash (control) or 100 μM NMDA for 120 seconds, alone (filled circles) or with inclusion of 300 μM sulfasalazine (open circles). $[Ca^{2+}]$, was analyzed in fluo-3-loaded neutrons immediately after treatment, mean ± S.E.M. (n÷55–94 randomly chosen neurons in 4–6 glass bottom dishes per condition), scaled to $[Ca^{2+}]$, after the sham control (÷100%). Asterisk indicates significant difference from relevant control (NMDA alone), at $\rho<0.05$ using ANOVA and Student-Neuman-Keuls' test.
Figure 5:
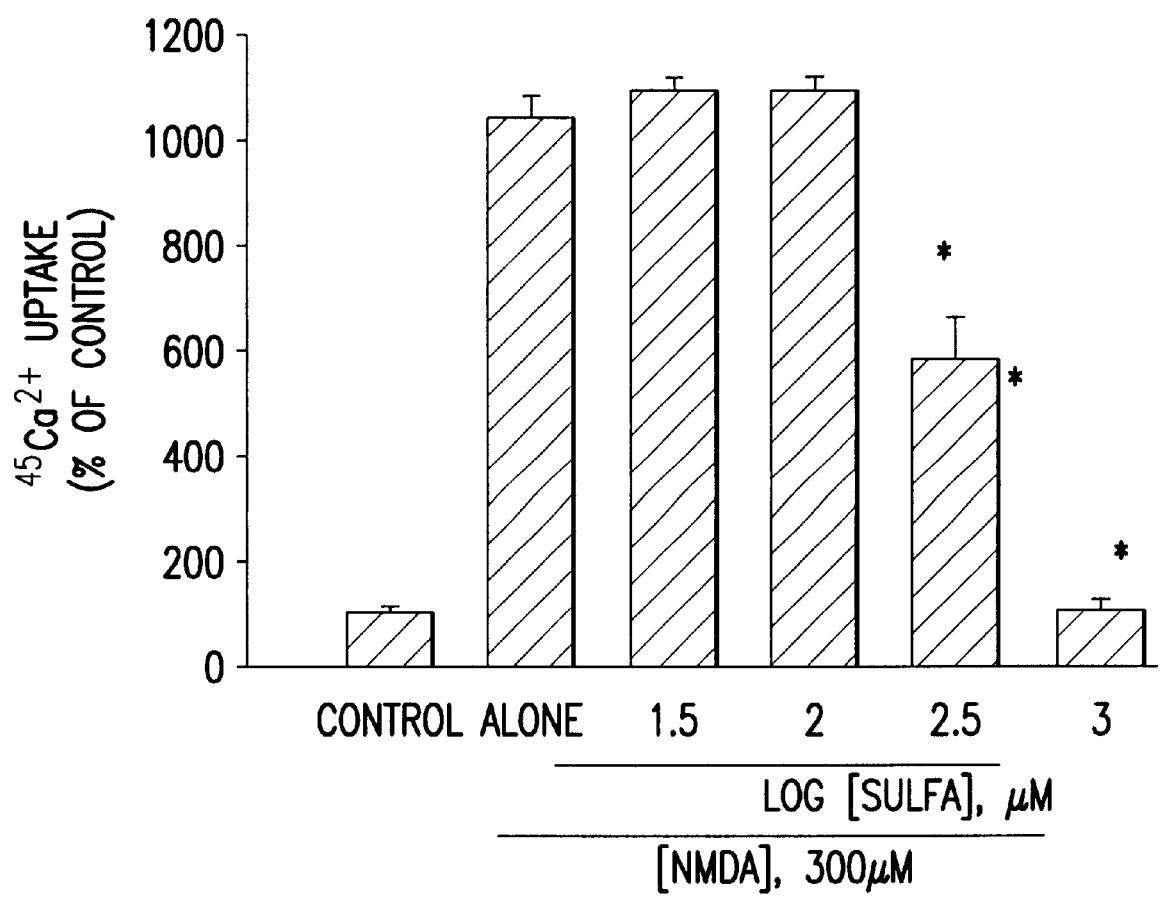
FIG. 5 is a graph plotting effects of sulfasalazine against NMDA-induced $^{45}Ca^{2+}$ uptake. Cortical cell cultrues (DIV 12–14) were exposed to a sham wash (control) or 300 μM NMDA, alone or in the presence of 30–1000 μM sulfasalazine. $Ca^{2+}$ influx was analyzed 10 min later by measuring $^{45}Ca^{2+}$ influx, mean ± S.E.M. (n=12 cultures per condition). Asterisk indicates significant difference from relevant control (NMDA alone), at $\rho<0.05$ using ANOVA and Student-Neuman-Keuls' test.

It has bee well documented that entry and accumulation of $Ca^{2+}$ is required for execution of NMDA-induced neuronal death (D. W. Choi J Neurosci 7:369–379, 1987). To examine the possibility that the neuroprotective effects of sulfasalazine against NMDA might be attributable to reducing $Ca^{2+}$ accumulation following exposure of cortical neurons to NMDA, intracellular $Ca^{2+}$ levels ($[Ca^{2+}]_i$) were analyzed using fluo-3 fluorescence dye specific for $Ca^{2+}$. Treatment with 300 µM NMDA resulted in immediate increase in $[Ca^{2+}]_i$ in cortical neurons (FIG. 4). NMDA-induced accumulation of $[Ca^{2+}]_i$ was markedly reduced in the presence of 300 μM sulfasalazine. Additional experiments were performed to determine if sulfasalazine would prevent $Ca^{2+}$ entry following activation of NMDA receptors. Influx of $^{45}Ca^{2+}$ was increased approximately 10-fold by 10 min after exposure to 300 μM NMDA (FIG. 5). This $^{45}Ca^{2+}$ influx was partially reduced with addition of 300 μM sulfasalazine and completely blocked with addition of 1000 μM sulfasalazine. Thus, sulfasalazine prevented NMDA neurotoxicity by interfering with entry and accumulation of $Ca^{2+}$ following activation of NMDA receptors.

Example 2. Sulfasalazine prevents free radical neurotoxicity.

Figure 6:
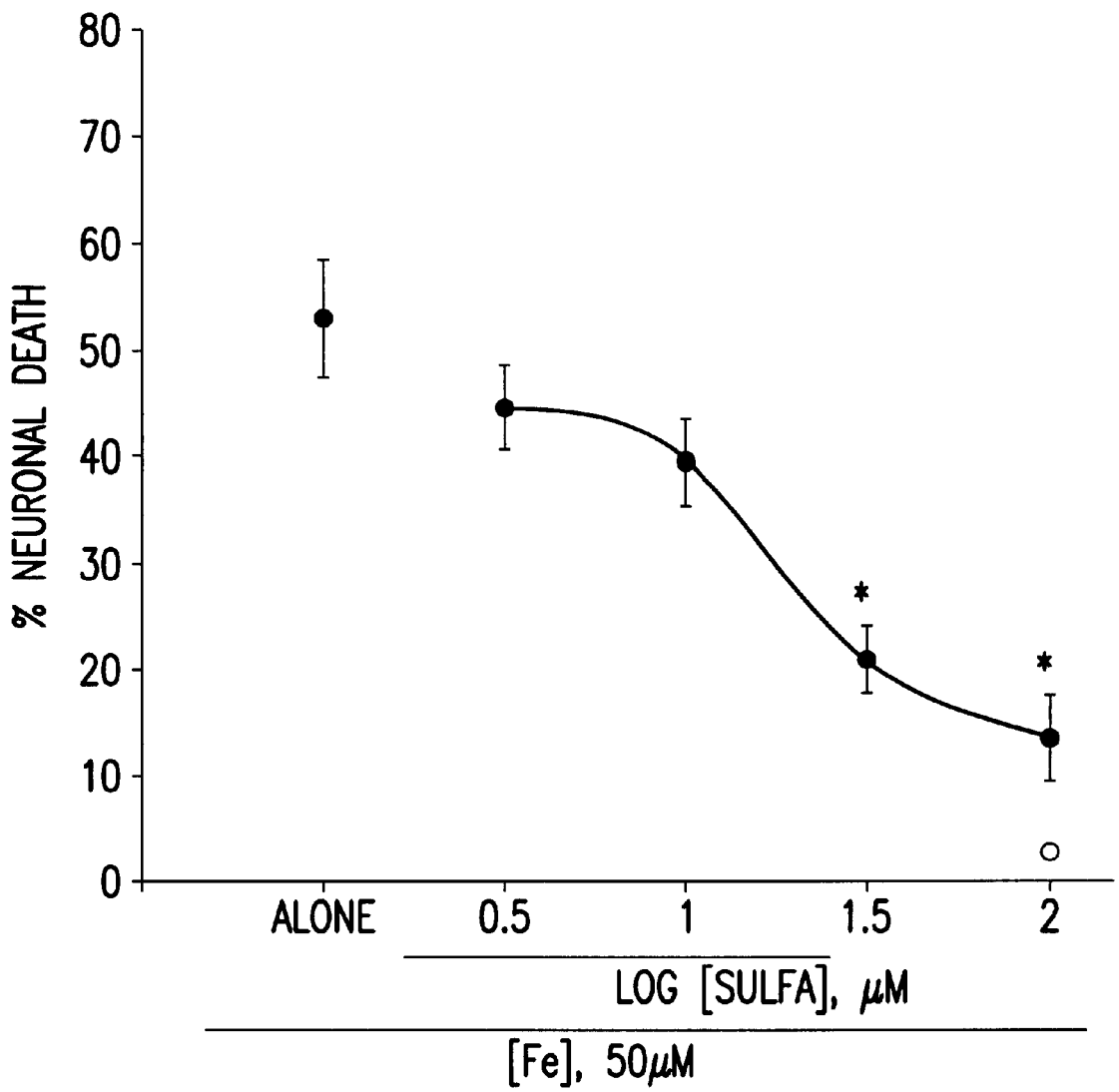
FIG. 6 is a graph plotting a dose-response effect of sulfasalazine against neuronal death following 24 hr-exposure to 50 μM $Fe^{2+}$. Cortical cell cultures (DIV 12–14) were exposed to 50 μM $Fe^{2+}$, alone or with 3–100 μM sulfasalazine. Neuronal death was assessed 24 hr later by measurement of LDH released into the bathing medium, means ± S.E.M. (n=4 12 culture wells per condition). Asterisk indicates significant difference from relevant control ($Fe^{2+}$ alone) at $\rho<0.05$, using ANOVA and Student-Neuman-Keuls' test.
Figure 7:
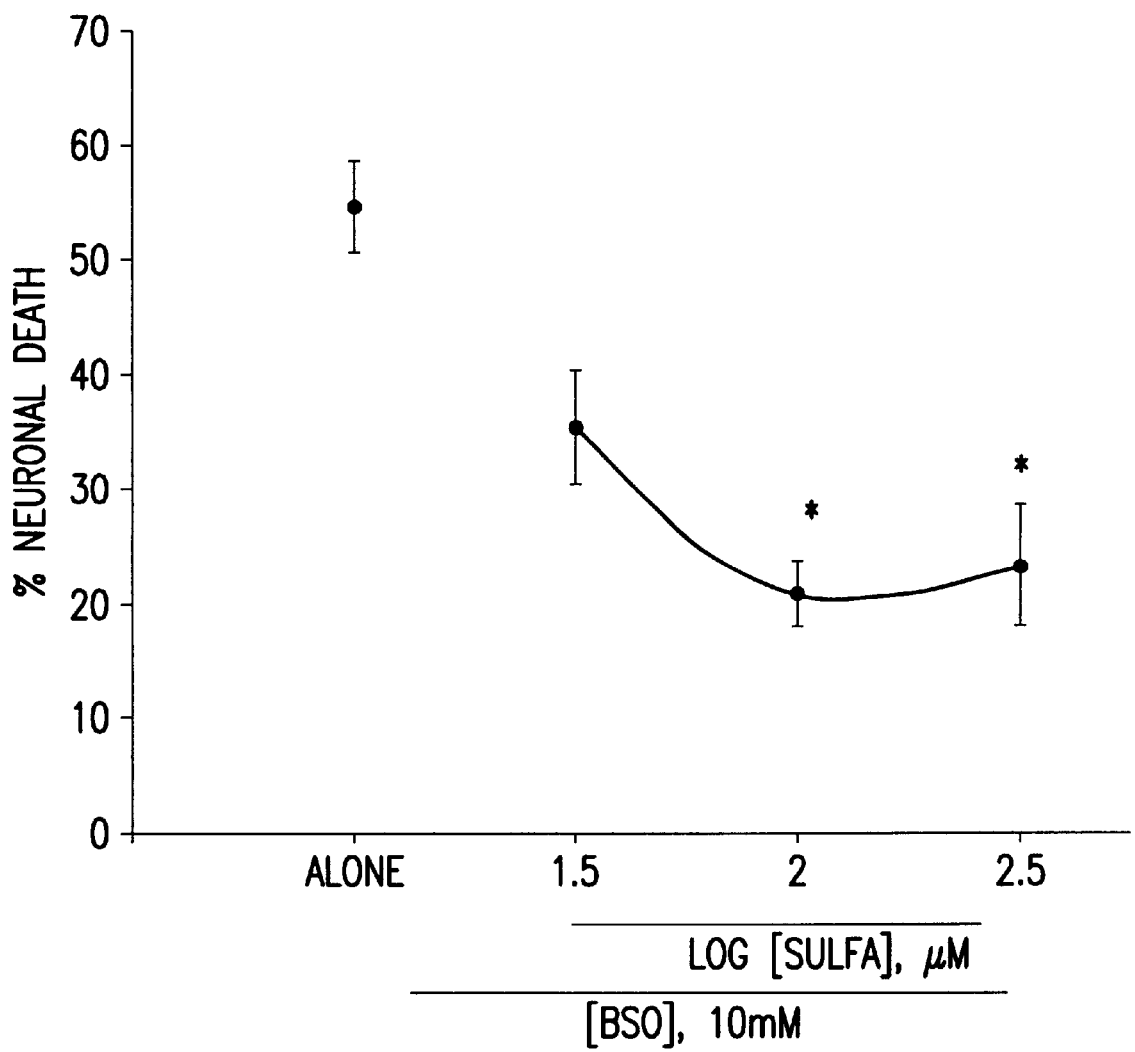
FIG. 7 is a graph plotting a dose-response effect of sulfasalazine against neuronal death following 24 hr-exposure to 10 mM BSO. Cortical cell cultures (DIV 12–14) were exposed to 10 mM L-buthionine-(S,R)-sulfoximine (BSO), alone or with 30–300 μM sulfasalazine. Neuronal death was assessed 24 hr later by measurement of LDH released into the bathing medium, mean ± SEM (n=8 culture wells per condition). Asterisk indicates significant difference from relevant control (BSO alone) at $\rho<0.05$, using ANOVA and Student-Neuman-Keuls' test.
Figure 8:
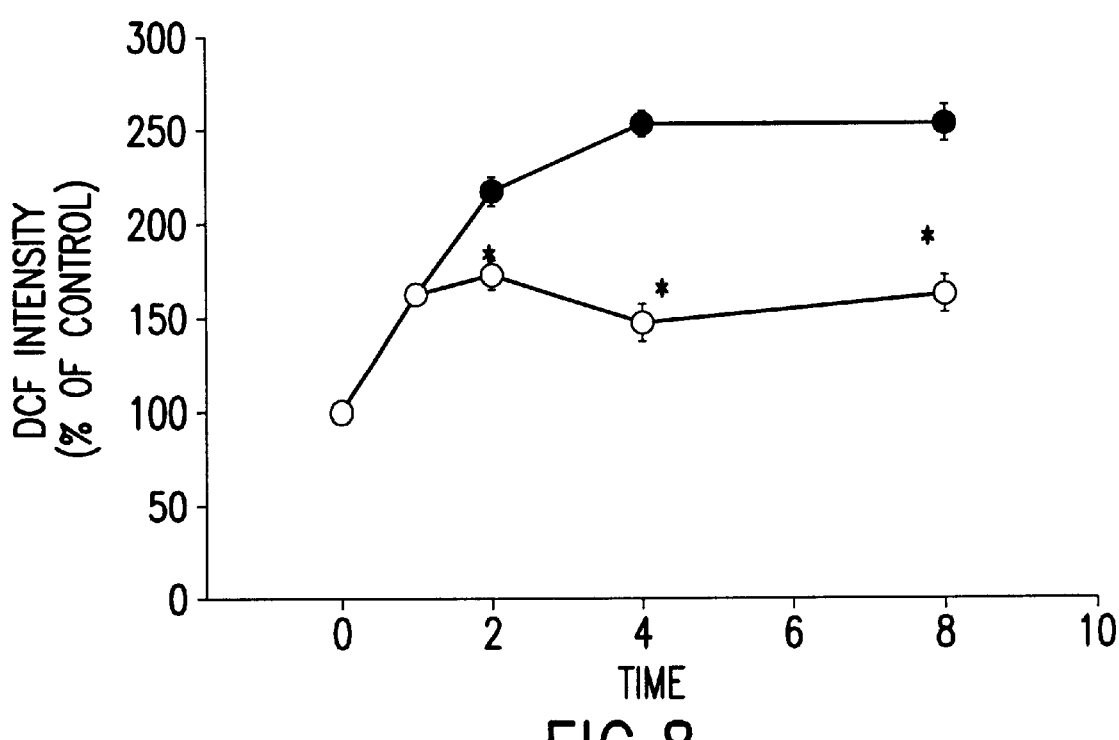
FIG. 8 is a graph plotting effects of sulfasalazine against $Fe^{2+}$-induced production of reactive oxygen species. Cortical cell cultures (DIV 13–14) were exposed to a sham wash (control) or 50 μM $Fe^{2+}$, alone or with 100 μM sulfasalazine for the indicated points of time. Levels of ROS in neurons were analyzed by monitoring the fluorescent signal of oxidized DCDHF, mean ± S.E.M. (n=53–80 neurons randomly chosen under a phase-contrast optic). Asterisk indicates significant difference from the relevant control ($Fe^{2+}$ alone in each time point) at $\rho<0.05$ using ANOVA and Student-Neuman-Keuls' test.

Cocultures of cortical neurons and glia (DIV 12–14) underwent free radical-mediated neuronal death 24 hr following exposure to 50 μM $Fe^{2+}$ (an agent producing hydroxyl radical via Fenton reaction) or buthionine sulfoximine (BSO, a glutathione-depleting agent). Concurrent addition of 30–300 μM sulfasalazine dose-dependently reduced neuronal death 24 hr following continuous exposure to $Fe^{2+}$ or BSO (FIGS. 6 & 7). Monitoring intracellular levels of reactive oxygen species (ROS) demonstrated that sulfasalazine reduced production of ROS following exposure to 50 μM $Fe^2$ (FIG. 8) Sulfasalazine protects cortical neurons from free radical injuries by scavenging ROS.

Example 3. Sulfasalazine attenuates $Zn^{2+}$ neurotoxicity.

Figure 9:
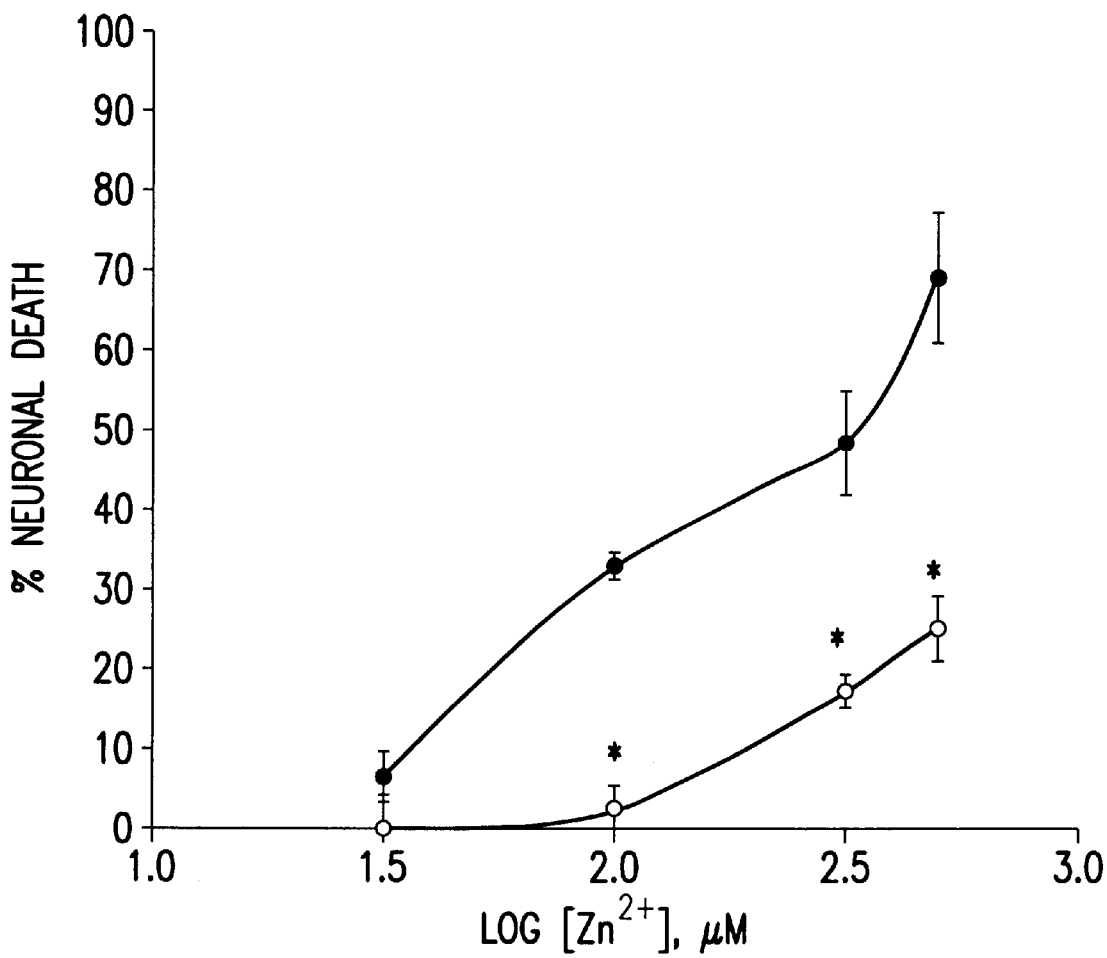
FIG. 9 is a graph plotting a dose-response effect of sulfasalazine against neuronal death 24 hr following exposure to 300 μM $Zn^{2+}$ for 30 min. Cortical cell cultures were exposed to 30–500 μM $Zn^{2+}$ for 30 min, alone (filled circles) or with inclusion of 100 μM sulfasalazine (open circles). Neuronal death was assessed 24 hr later by measurement of LDH released into the bathing medium, mean ± SEM (n=8 culture wells per condition). Asterisk indicates significant difference from relevant control ($Zn^{2+}$ alone) at $\rho<0.05$, using ANOVA and Student-Neuman-Keuls' test.
Figure 10:
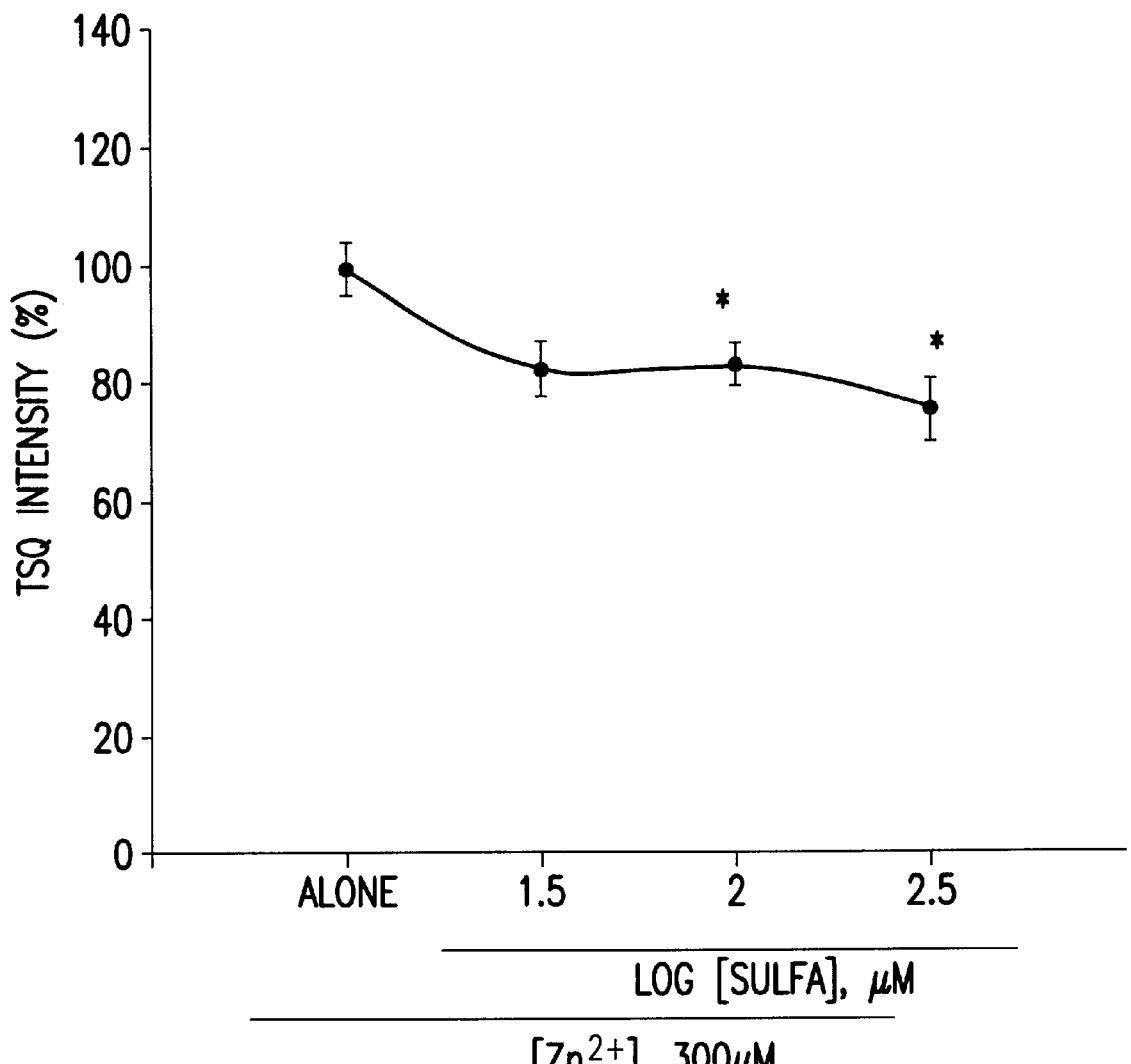
FIG. 10 is a graph plotting effects of sulfasalazine reducing $Zn^2$ entry into cortical cells. Sister cultures were exposed to 300 μM $Zn^{2+}$ for 30 min, alone or with inclusion of 30–300 μM sulfasalazine. $Zn^{2+}$ entry was assessed 30 min later by measuring fluorescence intensity of TSQ, a $Zn^{2+}$ chelating agent. (n=8 culture wells per condition). Asterisk indicates significant difference from relevant control ($Zn^2$ alone) at $p<0.05$, using ANOVA and Student-Neuman-Keuls' test.

Cortical cell cultures exposed to 300 μM $Zn^{2+}$ for 30 min underwent neuronal cell necrosis over the next 24 hr. Concurrent treatment with 10–100 μM sulfasalazine reduced $Zn^{2+}$ neurotoxicity in a dose-dependent manner (FIG. 9). This neuroprotective effect of sulfasalazine against $Zn^{2+}$ may be explained by anti-oxidant property of sulfasalazine as ROS was shown to mediate $Zn^{2+}$ neurotoxicity (Kim E Y, Koh J Y, Kim Y H, Sohn S, Joe E, Gwag B J, 1999, Eur J Neurosci. 11:327–334). However, we have reasoned that sulfasalazine may interfere with $Zn^{2+}$ entry. To test this possibility, $Zn^{2+}$ entry was analyzed using TSQ, a fluorescent dye specific for $Zn^{2+}$. The fluorescent signal of TSQ was manifest within 30 min after exposure of cortical cell cultures to 300 μM $Zn^{2+}$ (FIG. 10). Inclusion of 300 μM sulfasalazine slightly but significantly reduced $Zn^{2+}$ entry. This implies that sulfasalazine attenuates $Zn^{2+}$ neurotoxicity in part via interfering with $Zn^{2+}$ entry into neurons.

Example 4. Sulfasalazine attenuates neuronal death following deprivation of oxygen and glucose.

Figure 11:
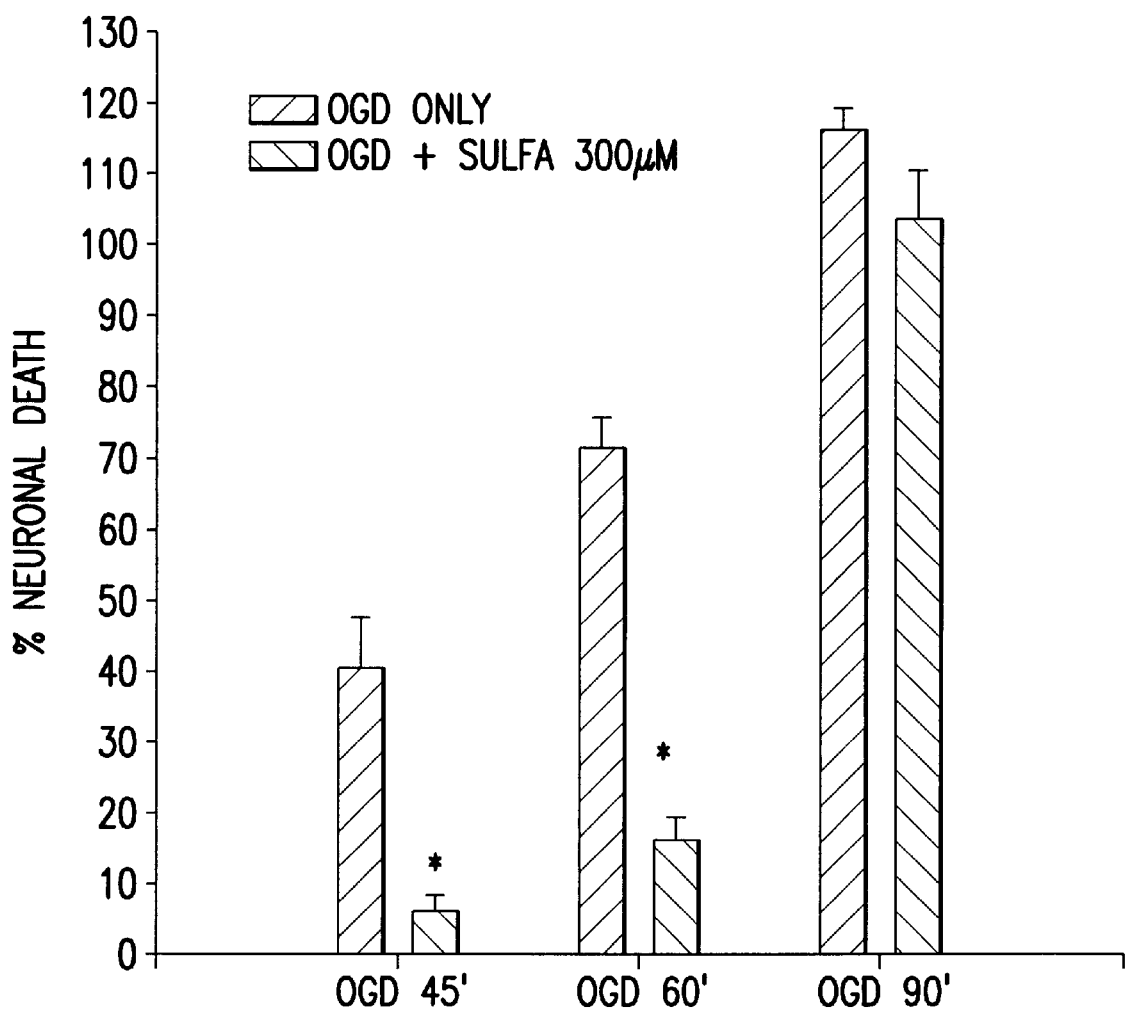
FIG. 11 is a graph plotting neuroprotective effects of sulfasalazine against deprivation of oxygen and glucose. Cortical cell cultures (DIV 14) were deprived of oxygen and glucose (OGD) for 45, 60 or 90 min, alone (black bars) or with inclusion of 300 $\mu$M sulfasalazine (gray bars). Neuronal death was assessed 24 hr later by measurement of LDH released into the bathing medium, mean ± SEM (n=4 culture wells per condition). Asterisk indicates significant difference from relevant control (OGD alone) at $p<0.05$, using ANOVA and Student-Neuman-Keuls' test.

Combined oxygen and glucose deprivation has been used to study mechanism and treatment of ischemic neuronal death (Goldberg and Choi, 1993, J Neurosci. 13:3510–3524). Cortical cell cultures deprived of oxygen and glucose for 45–90 min underwent 40–100% neuronal death over the next 24 hr. Inclusion of 300 μM sulfasalazine markedly reduced neuronal death following deprivation of oxygen and glucose for 45–60 min (FIG. 11). When deprivation of oxygen and glucose was extended to 90 min, the neuroprotective effects of sulfasalazine were decreased possibly due to appearance of AMPA/kainate neurotoxicity and apoptosis following prolonged deprivation of oxygen and glucose.

All documents cited in the specification and as references below are hereby incorporated in their entirety by reference.

Though the present invention has been described with regard to its preferred embodiments, one skilled in the art will appreciate from a reading of this disclosure that various changes in form and detail can be made without departing from the scope and spirit of the invention.

REFERENCES

A. I. Faden. *Pharmacol.Toxicol.* 78(1):12–17, 1996.
C. K. Joo, J. S. Choi, H. W. Ko, K. Park, S. Sohn, M. H. Chun, Y. J. Oh and B. J. Gwag. IOVS (16) 43:22, 1999.
D.E. Bredesen, M. Wiedau-Pazos, J. J. Goto, S. Rabizadeh, J. A. Roe, E. B. Gralla, L. M. Ellerby, and J. S. Valentine. *Neurology* 47:S36–8, 1996.
J. W. Olney. *Retina* 2:341–359, 1982.
D. W. Choi and J. Y. Koh. *Annv. Rev. Neurosci.* 21:347–75:347–375, 1998.
D. W. Choi. *Neuron* 1:623–634, 1988.
F. D. Hall, J. M. Braughler, and J. M. McCall. *J. Neurotrauma.* 5(1):81–89, 1988.
E. Y. Kim, J. Y. Koh, Y. H. Kim, S. Sohn and B. J. Gwag. Eur. J Neurosci. 11:327–334, 1999
J. L. Montastrue, O. Rascol, and J. M. Senard. *Neurosci. Biobehav. Rev* 21 (4):477–480, 1997.
K. A. Jellinger and C. Bancher, *J. Neural Transm. Suppl* 54:77–95:77–95, 1998.
M. F. Beal. *Ann. Neurol.* 38 (3):357–366, 1995.
M. P. Cuajungeo and G. J. Lees. *Brain Res. Rev.* 23 (3):219–236, 1997.
P. H. Chan. *Stroke* 27 (6):1124–1129, 1996.
S. J. Won, E. C. Park, B. R. Ryu,H. W. Ko, S. Sohn, H. J. Kwon, and B. J. Gwag, *Neurobiology of Disease* (in press), 2000.
Lee, J. M., G. J. Zipfel, and D. W. Choi, The changing landscape of schaemic brain injury mechanisms. Nature 399:7–14, 1999.
Minta, A, J. P. Kao, and R. Y. Tsien. Fluorescent indicators for cytosolic calcuim based on rhodamine and fluorescein chromophores. J. Biol. Chem. 264:8171–8178, 1989.
Mochizuki, H., Goto. K., Mori, H., and Mizuno, Y. Histochemical detection of apoptosis in Parkinson's disease. J. Neurol. Sci. 137:120–123, 1996.

What is claimed is:

1. A method for protecting central neurons from acute or chronic injuries to central nervous system (CNS), which comprises administering appropriate quantity and forms of sulfasalazine to a patient or a mammal suffering CNS injuries wherein said CNS injuries are caused by at least one selected from the group consisting of activation of ionotropic glutamate receptors sensistive to N-methyl-D-aspartate (NMDA); and $Zn^{2+}$ entry and accumulation following CNS injuries.

2. A method of claim 1, wherein said CNS injuries result from the activation of ionotropic glutamate receptors sensitive to N-methyl-D-aspartate (NMDA) after ischemia, hypoxia, hypoglycemia, traumatic brain injury, traumatic spinal cord injury, epilepsy, Huntington's disease, Parkinson's disease, or Amyotrophic lateral sclerosis.

3. A method of claim 1, wherein said sulfasalazine prevents influx and accumulation of $Ca^{2+}$ following activation of NMDA receptors.

4. A method of claim 1, wherein said CNS injuries are caused by said $Zn^{2+}$ entry and accumulation.

5. A method of claim 1, wherein said sulfasalazine interferes with $Zn^{2+}$ entry and accumulation.

6. A method of claim 1, wherein said CNS injuries results from hypoxic-ischemia.

7. A method of claim 6, wherein said neurons undergo degeneration following deprivation of oxygen and glucose.

8. A method of claim 7, wherein effects of sulfasalazine attenuating NMDA are responsible for reducing neuronal injury following deprivation of oxygen and glucose.

9. A method for reducing neuronal death in CNS injuries turning to unique property of sulfasalazine that prevents NMDA- or, $Zn^{2+}$-, and free radical-mediated neurotoxicity simultaneously.

10. A method for protecting central neurons from acute or chronic injuries to the central nervous system (CNS), which comprises administering appropriate quantity and forms of sulfasalazine to a patient or a mammal suffering CNS injuries, wherein sulfasalazine inhiits said CNS injuries caused by excess activation of ionotropic glutamate receptors sensitive to N-methyl-D-asparte (NMDA) following CNS injuries.

11. A method for protecting central neurons from acute or chronic injuries to the central nervous system (CNS), which comprises administering appropriate quantity and forms of sulfasalazine to a patient or a mammal suffering CNS injuries, wherein sulfasalazine inhiits said CNS injuries caused $Zn^{2+}$ entry and accumulation following CNS injuries.

* * * * *